United States Patent
Okawa et al.

(10) Patent No.: US 6,605,288 B1
(45) Date of Patent: Aug. 12, 2003

(54) DEODORANT COMPOSITION

(75) Inventors: Masayuki Okawa, Tochigi (JP); Kazuya Otsuji, Tochigi (JP); Hiroshi Sonohara, Wakayama (JP); Masako Isemura, Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/646,916

(22) PCT Filed: Nov. 12, 1999

(86) PCT No.: PCT/JP99/06345

§ 371 (c)(1),
(2), (4) Date: Oct. 12, 2000

(87) PCT Pub. No.: WO00/37036

PCT Pub. Date: Jun. 29, 2000

(30) Foreign Application Priority Data

Dec. 18, 1998 (JP) ............................................. 10-361595

(51) Int. Cl.⁷ .................................................. A61K 7/32
(52) U.S. Cl. .......................................... 424/401; 424/65
(58) Field of Search ................................ 424/401, 465

(56) References Cited

U.S. PATENT DOCUMENTS

| | | |
|---|---|---|
| 4,708,863 A | 11/1987 | Bews et al. |
| 5,534,246 A | 7/1996 | Herb et al. |

FOREIGN PATENT DOCUMENTS

| | | |
|---|---|---|
| EP | 0 024 175 | 2/1981 |
| EP | 0 435 438 | 7/1991 |
| EP | 0 435 483 | 7/1991 |
| EP | 0 676 192 | 10/1995 |
| EP | 0 676 193 | 10/1995 |
| FR | 0 858797 A1 | 2/1998 |
| JP | 56-39010 | 4/1981 |
| JP | 56-39011 | 4/1981 |
| JP | 62-212315 | 9/1987 |
| JP | 3-191731 | 8/1991 |
| JP | 4-65312 | 3/1992 |
| JP | 4-159204 | 6/1992 |
| JP | 4-316514 | 11/1992 |
| JP | 6-183943 | 7/1994 |
| JP | 6-240579 | 8/1994 |
| JP | 7-138140 | 5/1995 |
| JP | 7-304642 | 11/1995 |
| JP | 10-158139 | 6/1998 |
| WO | WO 87/04341 | 7/1987 |
| WO | WO 98/56890 | 12/1998 |

OTHER PUBLICATIONS

Patent Abstracts of Japan, JP 6–240579, Aug. 30, 1994.
Patent Abstracts of Japan, JP 62–212315, Sep. 18, 1987.

*Primary Examiner*—Thurman K. Page
*Assistant Examiner*—Michael A. Williamson
(74) *Attorney, Agent, or Firm*—Oblon, Spivak, McClelland, Maier & Neustadt, P.C.

(57) ABSTRACT

A deodorant composition comprising 0.03 to 5% by weight of a water-soluble metal salt, 0.01 to 5% by weight of a nonionic surface active agent, 0.1 to 10% by weight of silicone oil, and the balance of water.

12 Claims, No Drawings

DEODORANT COMPOSITION

TECHNICAL FIELD

The present invention relates to a deodorant composition which has excellent deodorizing effects on the odors of armpits, foot and the body of humans, the odors of animals, etc. to give comfort after use.

BACKGROUND ART

Many of conventionally proposed deodorants are effective on limited sites of application or limited substances as described, e.g., in Japanese Patent Application Laid-Open Nos. 191731/91 and 138140/95. There has been an increasing demand for a deodorant effective on a variety of substances giving off odors, e.g., on the odors of armpits, foot or hair of humans or the odors of animals, etc. In particular, where animals such as dogs, which have a strong smell, are kept as a domestic pet, removal of their odor is inevitable. Since shampooing an animal is too troublesome to do so frequently, a deodorant capable of easily deodorizing instead of shampooing has been awaited.

DISCLOSURE OF THE INVENTION

Accordingly, an object of the present invention is to provide a deodorant composition having excellent deodorizing effects on the odors of the armpits, foot and body of humans, the odors of animals, etc.

The present inventors have found that the above object is accomplished by an aqueous deodorant composition comprising specific amounts of a water-soluble metal salt, a nonionic surface active agent and silicone oil.

The present invention has achieved the above object by providing a deodorant composition comprising 0.03 to 5% by weight of a water-soluble metal salt, 0.01 to 5% by weight of a nonionic surface active agent, 0.1 to 10% by weight of silicone oil, and the balance of water.

BEST MODE FOR CARRYING OUT THE INVENTION

The metal salt which can be used in the deodorant composition of the present invention (hereinafter sometimes referred to as component (a)) is water-soluble, preferably having a solubility of 0.1 g/100 g-water or more at 25° C. Metals which constitute the metal salt include those forming mono- to trivalent cations, preferably alkali metals, alkaline earth metals, the group IIIA metals and transition metals of the fourth period of Periodic Table. The alkali metals include sodium and potassium. The alkaline earth metals include magnesium and calcium. The group IIIA metals include aluminum. The transition metals of the fourth period of Periodic Table include iron, copper, and zinc.

The salts constituting the metal salts include those forming mono- to trivalent anions. Chlorides, hydroxides, carbonic acid compounds and the like are particularly preferred.

Specific preferred examples of the metal salts are calcium chloride, aluminum chloride, magnesium chloride, sodium hydroxide, calcium hydroxide, potassium carbonate, sodium carbonate, magnesium carbonate, and so forth. These metal salts may be used as a combination of two or more thereof.

The amount of the metal salt to be compounded into the deodorant composition of the present invention is from 0.03 to 5% by weight, preferably 0.1 to 3% by weight, still preferably 0.3 to 1% by weight. If the amount of the metal salt is less than 0.03% by weight, deodorizing effects are not obtained. If it exceeds 5% by weight, crystals are precipitated appreciably after drying, resulting in a powdered state.

The nonionic surface active agent (hereinafter sometimes referred to as component (b)) includes those safe for human and animal bodies. In particular, fatty acid ester type nonionic surface active agents, polyoxyalkylene type nonionic surface active agents, alkylalkanolamide type nonionic surface active agents and alkyl glucoside type nonionic surface active agents are preferably used. The amount of the surface active agent to be compounded into the deodorant composition of the present invention is from 0.01 to 5% by weight, preferably 0.03 to 3% by weight, still preferably 0.04 to 0.5% by weight. If the amount of the nonionic surface active agent is less than 0.01% by weight, the ability to emulsify sebum, etc. is insufficient for component (a) to be bound to odor substances, resulting in reduction of the deodorizing effects. If it exceeds 5% by weight, the excess surface active agent causes stickiness after drying. These nonionic surface active agents can be used as a combination of two or more thereof.

The fatty acid ester type nonionic surface active agents include esters between polyhydric alcohols and fatty acids. The polyhydric alcohols include alkylene glycols, such as ethylene glycol, propylene glycol, and 1,4-butylene glycol, glycerol, pentaerythritol, sorbitol, sorbitan and sucrose. The fatty acids include those having 8 to 18 carbon atoms, such as lauric acid, myristic acid, palmitic acid, stearic acid, and oleic acid.

Examples of preferred fatty acid ester type nonionic surface active agents are glycerol mono-oleate, sorbitan mono-oleate, coconut oil fatty acid sorbitan, sorbitan mono-oleate, and sorbitan trioleate.

The polyoxyalkylene type nonionic surface active agents are nonionic surface active agents having a polyoxyalkylene chain in the molecule thereof. The oxyalkylene group constituting the polyoxyalkylene chain includes an oxyethylene group, an oxypropylene group, and combinations thereof, with an oxyethylene group being particularly preferred. The polyoxyalkylene type nonionic surface active agents include polyalkylene glycols, such as polyoxyethylene polyoxypropylene glycol; ethers of polyalkylene glycols and fatty acid-polyhydric alcohol esters, such as polyoxyethylene sorbitan fatty acid esters, polyoxyethylene sorbitol tetra-oleate, polyethylene glycol fatty acid esters, and polyoxyethylene hydrogenated castor oil; ethers of polyalkylene glycols and aliphatic alcohols, such as polyoxyethylene alkyl ethers; and ethers of polyalkylene glycols and aromatic alcohols, such as polyoxyethylene alkylphenyl ethers.

Preferred examples of the polyoxyalkylene type nonionic surface active agents are polyoxyethylene sorbitan coconut oil fatty acid esters, polyoxyethylene sorbitan mono-oleate, polyoxyethylene sorbitan tetra-oleate, polyoxyethylene lauryl ether, and polyethylene glycol mono-stearate.

The alkylalkanolamide type nonionic surface active agents include compounds represented by general formula: $RCON[(CH_2)_n-OH]_2$, wherein R represents an alkyl group which preferably has 8 to 18, particularly 8 to 14, carbon atoms; and n represents the number of carbon atoms of the alkanol group, preferably 2 to 4.

Preferred examples of the alkylalkanolamide type nonionic surface active agents include palm kernel oil fatty acid diethanolamide.

The alkyl glucoside type nonionic surface active agents include those represented by $R'(OR'')_xOG_y$. In the formula, R' represents a straight-chain or branched alkyl, alkenyl or alkylphenyl group or a mixture thereof, with an alkenyl group having one unsaturated bond being preferred. The carbon atom number of these groups is preferably 8 to 18, particularly 8 to 12. R'' represents an alkylene group, of which the carbon atom number is preferably 2 to 4. G represents a residual group derived from a reducing sugar. X is preferably a number averaging 0 to 10, and Y is preferably a number averaging 1 to 10.

Preferred examples of the alkyl glucoside type nonionic surface active agents include lauryl glucose, oleyl glucose, and coconut oil fatty acid glucose.

The silicone oil (hereinafter sometimes referred to as component (c)) includes polysiloxanes. Specific examples of the polysiloxanes include dimethyl polysiloxane and methylhydrogen polysiloxane. Various modified silicone oils, such as fluoro-modified silicone oil, amino-modified silicone oil, epoxy-modified silicone oil, alcohol-modified silicone oil, and alkyl-modified silicone oil, are also employable, but it is preferred to use unmodified silicone oil from the standpoint of safety for human bodies and animals. The above-described silicone oils can be used as a combination of two or more thereof.

In using a polysiloxane as silicone oil, it is preferred for the silicone oil to have a degree of polymerization of 30 to 20000, particularly 80 to 3000, so as to have a low viscosity easy to handle in the preparation of the deodorant composition or in use and to impart a smooth feel to the skin or hair.

The amount of the silicone oil to be compounded into the deodorant composition of the present invention is from 0.1 to 10% by weight, preferably 0.2 to 5% by weight, still preferably 0.5 to 3% by weight. If the amount of the silicone oil is less than 0.1% by weight, the skin or hair is not given a smooth feel. If it is more than 10% by weight, the composition is sticky and takes time to dry.

The amounts of components (a), (b) and (c) to be compounded are as described above. From the viewpoint of obtaining a low viscosity and maintaining stability, it is preferred that the weight ratio of component (a) to component (b) be 0.06 to 50, particularly 1 to 10, and that of component (a) to component (c) be 0.003 to 50, particularly 0.01 to 0.1.

The deodorant composition according to the present invention is an aqueous composition comprising the above-described components (a) to (c) in the above-described compounding ratio and the balance of water.

If necessary, the deodorant composition of the present invention can contain antiseptics such as a p-hydroxybenzoate, lower alcohols such as ethanol, perfumes, buffering agents, and the like in addition to the above-described components. These components are each preferably added in an amount of 0.01 to 10% by weight, particularly 0.03 to 5% by weight, to manifest their effects adequately.

The deodorant composition of the present invention is used to remove the odors of the armpits, foot, hair and body of humans and the odors of animals, etc. It is known that animals such as dogs give off strong odors (odors of the body, mouth and earwax). The deodorant composition of the present invention exhibits extremely high deodorizing effects on such animal odors. The deodorant composition of the present invention shows extremely high deodorizing effects even on the strong odors of dogs. Besides, the deodorizing effects are not temporary but of long duration.

The deodorant composition of the present invention is applied to a site to be deodorized by scattering or spraying an adequate amount of the composition and distributing the applied composition evenly over the site by hand or with a tool such as a brush, followed by spontaneous drying or by brushing a site to be deodorized with a brush to which an adequate amount of the composition has been applied by scattering or spraying, followed by spontaneous drying, whereby the deodorizing effects are exerted and, in addition, a smooth feel is imparted to the site. When, in particular, the deodorant composition of the present invention is applied to the hair of humans or animals, the hair becomes smooth to brush or comb. Accordingly, the deodorant composition of the present invention is also suited as a deodorant shampoo needing no wipe.

It is preferred that the deodorant composition of the present invention has a viscosity of 1 to 50 mPa.s, particularly 1 to 5 mPa.s, at 20° C. to be atomized satisfactorily and to be easy to handle when applied with a trigger spray, etc. The viscosity is measured with a Brookfield viscometer equipped with a BL adaptor at 60 rpm.

While not particularly limited, the pH of the deodorant composition of the present invention is preferably 4 to 7 for the safety for human and animal bodies. Useful pH adjustors include phosphoric acid, lactic acid, and citric acid.

Examples 1 to 6 and Comparative Examples 1 to 4

The components shown in Table 1 were compounded in the amounts shown in the table to prepare an aqueous composition. The resulting compositions were evaluated for deodorizing effect, feel of use (a smooth feel to the touch and smoothness in combing), and drying properties in accordance with the following methods. The results obtained are shown in Table 1.

Deodorizing Effect

One gram of the composition was dropped on 0.3 g of dead hair of a dog, mixed well, and dried spontaneously. An organoleptic test by 10 panel members was conducted. The standards of evaluation are as follows.

A The average of the scores given by 10 panel members exceeds 3.

B The average of the scores given by 10 panel members is greater than 2 and not greater than 3.

C The average of the scores given by 10 panel members is greater than 1 and not greater than 2.

D The average of the scores given by 10 panel members is 1 or smaller.

Each panel members was asked to score based on the following criteria.

4 Odorless
3 Slight odor
2 Easily perceptible odor
1 Strong odor
0 Very strong odor Feel of Use
(1) Smooth Feel A 1 cm by 4 cm piece of dog's skin was soaked in the composition, taken out, dried spontaneously and subjected to an organoleptic test by 10 panel members. The standards of evaluation are as follows.

A The average of the scores given by 10 panel members exceeds 3.

B The average of the scores given by 10 panel members is greater than 2 and not greater than 3.

C The average of the scores given by 10 panel members is greater than 1 and not greater than 2.

D The average of the scores given by 10 panel members is 1 or smaller.

Each panel members was asked to score based on the following criteria.

4 The treatment gives a very good smooth feel.
3 The treatment gives a good smooth feel.
2 The treatment gives an obvious smooth feel.
1 The treatment gives a slight smooth feel.
0 The treatment results in no difference in smooth feel.

(2) Smoothness in Combing

Simultaneously with the above-described evaluation of the smooth feel, the 10 panel members combed the dog's skin with a comb (#12, available from Champion Kengu K.K.) to organoleptically evaluate smoothness in combing according to the following standards.

A The average of the scores given by 10 panel members exceeds 3.
B The average of the scores given by 10 panel members is greater than 2 and not greater than 3.
C The average of the scores given by 10 panel members is greater than 1 and not greater than 2.
D The average of the scores given by 10 panel members is 1 or smaller.

Each panel members was asked to score based on the following criteria.

4 The treatment results in drastic improvement.
3 The treatment results in considerable improvement.
2 The treatment results in obvious improvement.
1 The treatment results in slight improvement.
0 The treatment results in no change.

Drying Properties

In the above-described evaluation of the smooth feel, the time required for the specimen taken out of the composition to dry spontaneously was compared according to the following criteria. The temperature and humidity were 25° C. and 65%.

A The specimen dries in less than 3 hours.
B The specimen dries in 3 hours or more and less than 4 hours.
C The specimen dries in 4 hours or more and less than 5 hours.
D The specimen remains undried for 5 hours or more.

As is apparent from the results shown in Table 1, it is seen that the compositions of Examples (the products of the present invention) produce higher deodorizing effects than the compositions of Comparative Examples and also give a smooth feel and make the hair smooth in combing after use.

INDUSTRIAL APPLICABILITY

The present invention provides a deodorant composition which has excellent deodorizing effects on the odors of armpits, foot and the body of humans, the odors of animals, etc. to give comfort after use.

The deodorant composition of the present invention exhibits extremely high deodorizing effects on the strong odors of animals.

The deodorant composition of the present invention is particularly useful as a deodorant shampoo composition which can be used for deodorizing human hair or animal hair and needs no wipe.

What is claimed is:

1. A deodorant composition comprising 0.03 to 5% by weight of a water-soluble metal salt, 0.01 to 5% by weight of a nonionic surface active agent, 0.1 to 10% by weight of silicone oil, and the balance of water, wherein said metal salt is a chloride, a hydroxide or a carbonic acid compound of sodium, potassium, magnesium, calcium, iron copper or zinc.

2. The deodorant composition according to claim 1, wherein said nonionic surface active agent is a fatty acid ester nonionic surface active agent, a polyoxyalkylene nonionic surface active agent, an alkylalkanolamide nonionic surface active agent or an alkyl glucoside nonionic surface active agent.

3. A deodorant composition as set forth in claim 1, wherein said metal salt is a chloride, hydroxide or carbonic acid compound of calcium or magnesium.

4. A deodorant composition as set forth in claim 1, wherein said metal salt is calcium chloride or calcium hydroxide.

TABLE 1

(unit: wt %)

| | | Example | | | | | | Comparative Example | | | |
|---|---|---|---|---|---|---|---|---|---|---|---|
| | | 1 | 2 | 3 | 4 | 5 | 6 | 1 | 2 | 3 | 4 |
| Component (a) | Calcium chloride | 0.1 | 0.5 | 0.5 | | | | 0.01 | 0.5 | 0.5 | 0.3 |
| | Calcium hydroxide | | | | 0.2 | 0.5 | | | | | |
| | Magnesium carbonate | | | | | | 0.1 | | | | |
| Component (b) | Alkyl glucoside[*1] | 0.03 | 0.05 | 0.1 | 1 | 0.1 | 1.5 | 1 | 0 | 0.2 | 0.3 |
| Component (c) | Dimethyl polysiloxane (n[*2] = 2700) | 0.5 | 0.7 | 1 | | | | 0.2 | 7 | 0.03 | 12 |
| | Methylhydrogen polysiloxane (n[*2] = 2500) | | | | 1.5 | 2 | 2.5 | | | | |
| Ethanol | | 5 | 5 | 5 | 5 | 5 | 5 | 5 | 5 | 5 | 5 |
| Methyl p-hydroxybenzoate (antiseptic) | | 0.3 | 0.3 | 0.3 | 0.3 | 0.3 | 0.3 | 0.3 | 0.3 | 0.3 | 0.3 |
| Water | | bal. | bal. | bal. | bal. | bal. | bal. | bal. | bal. | bal. | bal. |
| Total | | 100 | 100 | 100 | 100 | 100 | 100 | 100 | 100 | 100 | 100 |
| Deodorizing effect | | B | A | A | B | A | B | D | C | B | B |
| Feel of use | Smooth feel | B | A | A | A | A | A | B | B | C | B |
| | Smoothness in combing | B | A | A | A | A | A | B | B | C | B |
| Drying properties | | B | B | B | B | B | B | B | B | B | C |

Note:
[*1]Mydol 12 (trade name), available from Kao Corp.
[*2]Degree of polymerization 5. A deodorant composition as set forth in claim 1, wherein said metal salt is magnesium carbonate.

6. A deodorant composition as set forth in claim 1 wherein said metal salt is magnesium chloride.

7. A method of removing the odor of armpits, foot, hair or body of a human or the odor of an animal comprising applying the deodorant composition set forth in claim 1 to a site to be deodorized, distributing the applied composition evenly over the site, and drying the composition spontaneously.

8. A method of removing the odor of armpits, foot, hair or body of a human or the odor of an animal comprising applying the deodorant composition set forth in claim 1 to a brush, brushing a site to be deodorized with the brush, and drying the composition spontaneously.

9. A method of removing the odor of animals, comprising applying the deodorant composition set forth in claim 1 to a brush, brushing a site to be deodorized with the brush, and drying the applied composition.

10. A method of removing the odor of animals, comprising applying the deodorant composition set forth in claim 1 to a site to be deodorized, distributing the applied composition evenly over the site, and drying the composition.

11. A method of removing the odor of animals, comprising applying the composition of claim 1 to the hair of an animal and combing or brushing the composition through the animal's hair.

12. A method of removing the odor of animals, comprising applying the composition of claim 1 to the hair of an animal and combing or brushing the composition through the animal's hair.

* * * * *